(12) United States Patent
Yom-Tov et al.

(10) Patent No.: US 9,427,185 B2
(45) Date of Patent: Aug. 30, 2016

(54) USER BEHAVIOR MONITORING ON A COMPUTERIZED DEVICE

(71) Applicant: Microsoft Corporation, Redmond, WA (US)

(72) Inventors: Elad Yom-Tov, Hoshaya (IL); Eric J. Horvitz, Kirkland, WA (US); Ryen William White, Redmond, WA (US); Munmun De Choudhury, Bellevue, WA (US); Scott J Counts, Seattle, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 16 days.

(21) Appl. No.: 13/922,375

(22) Filed: Jun. 20, 2013

(65) Prior Publication Data

US 2014/0377727 A1 Dec. 25, 2014

(51) Int. Cl.
*A61B 5/16* (2006.01)
*G06F 19/00* (2011.01)
*A61B 5/00* (2006.01)

(52) U.S. Cl.
CPC ........... *A61B 5/165* (2013.01); *G06F 19/3437* (2013.01); *A61B 5/4803* (2013.01); *A61B 2562/0204* (2013.01); *G06F 19/345* (2013.01)

(58) Field of Classification Search
CPC .......... A61B 1/00; A61B 5/00; A61B 5/165; A61B 5/4803; A61B 2562/0204; G06F 19/3437; G06F 19/345
See application file for complete search history.

(56) References Cited

U.S. PATENT DOCUMENTS

| 8,540,516 B2* | 9/2013 | Williams et al. ............. 434/236 |
| 2002/0106617 A1* | 8/2002 | Hersh ...................... G09B 7/02 434/236 |
| 2007/0100804 A1* | 5/2007 | Cava ................... G06F 17/3064 |
| 2008/0118899 A1* | 5/2008 | Sahakian et al. ............. 434/236 |
| 2012/0077160 A1* | 3/2012 | DeGutis et al. ............. 434/236 |
| 2014/0370469 A1* | 12/2014 | Krystek .............. A47L 15/0063 434/236 |

* cited by examiner

*Primary Examiner* — Timothy A Musselman
(74) *Attorney, Agent, or Firm* — Alin Corie; Sandy Swain; Micky Minhas

(57) ABSTRACT

The subject disclosure is directed towards monitoring user behavior on a computerized device for any deviation from normal or acceptable behavior that is likely to affect the user's mental state. A prediction model corresponding to features of one or more mental states may be compared with features based upon current user behavior. If the user's current behavior presents a mental state indicative of an uncharacteristic deviation from the normal or acceptable behavior, descriptive data associated with that mental state may be presented to the user in addition to a trusted individual, such as a health care professional.

20 Claims, 8 Drawing Sheets

USER BEHAVIOR MONITORING ON A COMPUTERIZED DEVICE

BACKGROUND

Mental illnesses, psychological disorders, and other mental health issues impede a quality of life for a considerable population. Often, healthcare professionals are not aware of a patient's experiencing episodes or symptoms until after the fact. The patient may only see his/her healthcare professional weekly or bi-weekly, for example. In order to provide the best care, some professionals are personal caregivers who treat patients in their own homes and occasionally live with them if needed. Personal caregivers, however, can be expensive and are not affordable by everyone. Other patients are monitored in a hospital or a facility by a team of professionals who often treat groups of patients with similar afflictions. For patients who desire a more typical lifestyle, this arrangement can be cumbersome and also expensive.

SUMMARY

This Summary is provided to introduce a selection of representative concepts in a simplified form that are further described below in the Detailed Description. This Summary is not intended to identify selected features or essential features of the claimed subject matter, nor is it intended to be used in any way that would limit the scope of the claimed subject matter.

Briefly, various aspects of the subject matter described herein are directed towards monitoring user behavior via a computerized device and alerting trusted individuals of user behavioral changes that are likely to affect the user's mental health. In one aspect, a classifier may be downloaded onto the user's computerized device and configured to run in the background. In another aspect, the classifier operates on a server as a network/cloud-based resource. The user's computerized device communicates user interaction to the classifier, which may or may not render a prediction as to the user's current or future mental state.

A hardware/software component referred to herein as a monitoring mechanism may invoke steps for automatically identifying and predicting behavior changes from current online activities and user interactions (e.g., queries and social media posts, resources accessed and so on). In one aspect, the monitoring mechanism may generate alerts for the pending behavior changes.

Other advantages may become apparent from the following detailed description when taken in conjunction with the drawings.

BRIEF DESCRIPTION OF THE DRAWINGS

The present invention is illustrated by way of example and not limited in the accompanying figures in which like reference numerals indicate similar elements and in which.

DETAILED DESCRIPTION

Figure 1:
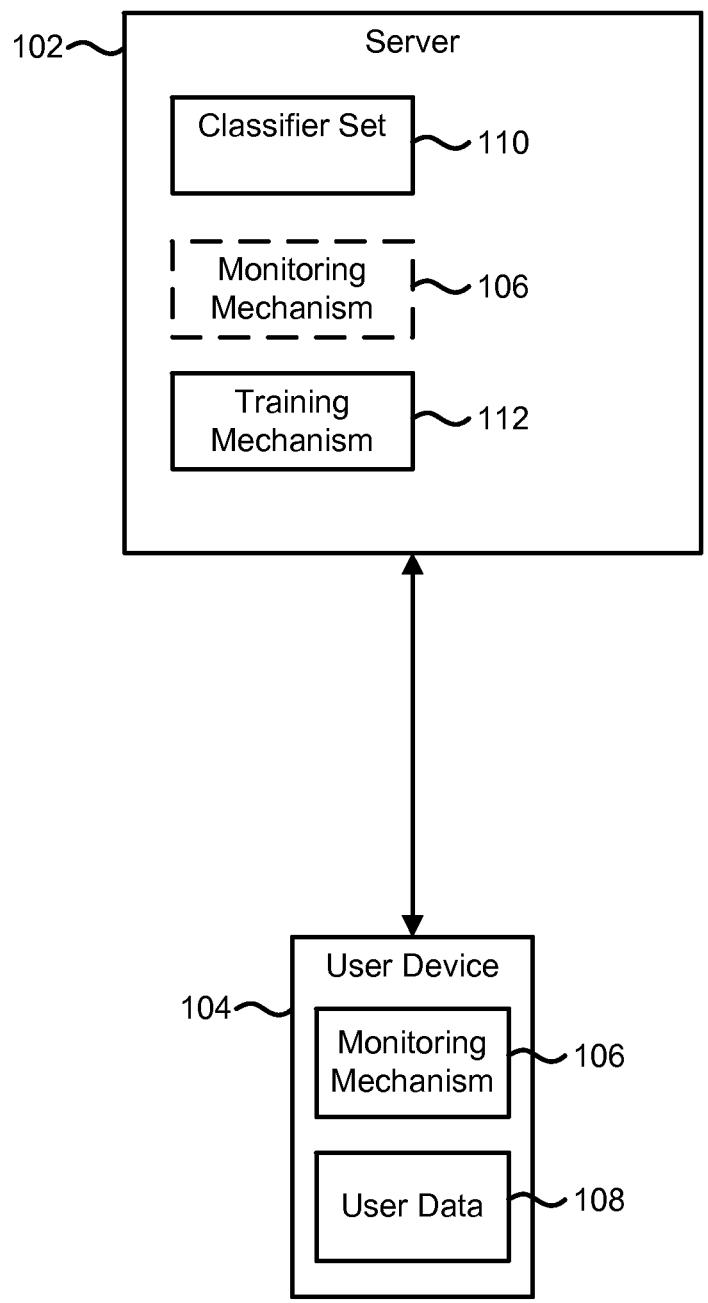
FIG. 1 is a block diagram illustrating an example system for monitoring user behavior according to one example implementation.

Various aspects of the technology described herein are generally directed towards monitoring mechanisms for predicting a user's mental state based upon extracted feature information. Mental health issues affect a significant number of people; developing systems to predict depressive or manic events may improve a quality of a person's life. As described herein, various user data, including user interactions with others and/or online activities, have various features of which some indicate a potential change in the user's behavior. If the extracted feature information satisfies certain conditions/expectations corresponding to a particular mental state, there is a high likelihood that the user is experiencing that mental state.

One example implementation of a monitoring mechanism includes at least a portion of an application made available for a download onto a desktop computer or mobile device, such as smartphone or a tablet. The monitoring mechanism uses a predictive model to identify changes to the user's online behavior, and when identified, alerts trusted individuals that potential mood shifts or other psychological disorders are likely to occur in the near future. This enables people to proactively improve their outcomes or to seek help from caregivers and medical professionals. As an alternative, the monitoring mechanism may be implemented at least in part as a cloud-based resource/service that renders predictions and/or communicates alerts over a network.

According to one example implementation, the monitoring mechanism within a user device adapts a prediction model to the user's behavior. The predictive model may be personalized or customized for the user's specific behavior by setting appropriate prediction model parameters for that user. For example, while in operation on the user's computerized device, the monitoring mechanism may be configured to establish a behavior baseline of feature information corresponding to normal or acceptable user behavior. In order to more accurately predict the user's mental state, including any mood disorder, the monitoring mechanism updates the predictive model using features extracted from interaction data (e.g., queries submitted to search engines, social media postings, and associated metadata). The user may explicitly consent to such data being collected during engagement with online properties.

The predictive model may use an initial model for predicting another user's mental state. While both users may share at least some similarity, such as demographics or mental illness, the other user may have a limited interaction history, whereby starting from an initial model is advantageous. Furthermore, the other user may adapt his or her instance of the predictive model. For example, when compared to previous online activities, recently logged online activities may include at least some selected features indicative of a change from the other user's normal behavior.

It should be understood that any of the examples herein are non-limiting. As such, the present invention is not limited to any particular embodiments, aspects, concepts, structures, functionalities or examples described herein. Rather, any of the embodiments, aspects, concepts, structures, functionalities or examples described herein are non-limiting, and the present invention may be used various ways that provide benefits and advantages in computing and health monitoring in general.

FIG. 1 is a block diagram illustrating an example system for monitoring user behavior according to one example implementation. Example components of the example system may include one or more computerized devices comprising a server 102 communicably coupled to a user device 104. One example implementation of the user device 104 stores a monitoring mechanism 106 and various user data 108.

The monitoring mechanism 106 generally refers to an application that may be downloaded and installed on the user device 104. This application may be an operating system component, such as a browser component. For example, the user may purchase or otherwise acquire such an application from an online marketplace. As another example, health care providers or insurance companies may provide the user with the application. The monitoring mechanism 106 may be configured with a combination of classifiers selected from a classifier set 110 as described herein.

The user data 108 as described herein may refer to historical behavior-related data, possibly collected over a substantial time period, including data corresponding to interactions between the user and other people or computers via the user device 104. Such interactions may manifest in different data formats, such as social media postings, search engine queries, and other online activities. The user data 108 also includes metadata associated with the above user interactions. For instance, the user data 108 may describe a series of search engine queries using related date/time information. The monitoring mechanism 106 may be configured to extract features from the user data 108 and establish a behavior baseline of feature information indicative of normal or acceptable user behavior. The user also may enter certain information, such as age, gender, information on life events (e.g., the birth of a child, the death of a loved one) and/or information regarding any diagnosed medical conditions. The user data 108 may also include information provided by the user on the time of previous events of interest, e.g., the time and date of previous manic events.

One example implementation of the server 102 stores classifiers in the classifier set 110 and a training mechanism 112. Each of these classifiers may be configured to predict a user's mental state based, at least in part, upon a change in the user's behavior as indicated by the user data 108. Mental states associated with the classifiers may range from depression and anxiety to anger and paranoia. The user's mental state may result from a psychological event. Psychological events include a type of life-affecting occurrence or action. By way of a few examples, these events include bouts of depression related to births or deaths of close family members, spousal divorce, job loss, critical injuries and/or the like. Other psychological events include anxiety linked to pending deadlines.

The monitoring mechanism 106 may define a behavior baseline using features indicative of the user's normal and/or acceptable psychological behavior. One example implementation includes a normalized feature distribution over the user data. An alternative implementation generates a feature distribution representing normal and/or acceptable behavior for an average member of a population, which may be establishing by aggregating user data from a significant number of volunteers. A statistically significant deviation from that behavior baseline indicates a number of possible psychological events. Some of these events may correspond to symptoms of a mental illness or a psychological disorder. For example, after a birth of a child, a mother may experience characteristics/features associated with postpartum depression; and her social media postings may exhibit at least some recognizable features. A model for predicting postpartum depression may include a decision tree or a utility function built from these features. The appearance of certain keywords, for example, keywords denoting depression, in the social media postings may represent a deviation from the behavior baseline. It is appreciated that embodiments described in the present disclosure may utilize other statistical/decision analysis techniques for modeling a psychological event.

The monitoring mechanism 106 may adapt the model to the behavior baseline by adjusting certain model elements (e.g., conditions of the decision tree). Such an adjustment customizes the model to the user's behavior and helps avoid false positives and false negatives. One example implementation configures the model with a temporal parameter and adjusts the model elements based upon some time value(s). As time elapses, some mental states are not likely to occur and therefore, certain model elements may change to reflect higher or lower thresholds. For example, predictions regarding postpartum depression gradually lose meaning after the child's birth and at some point, may no longer be possible.

As another example, viewing web pages provided by a mental health information portal also may correspond to a behavior change. By viewing such content, the user may have already experienced a psychological event and is seeking at least some form of professional help or, alternatively, the user may be likely to experience a psychological event capable of affecting the user's mental state. Other page viewing features may indicate user behavioral changes, such as dramatic changes in Internet browsing behavior. If a person who usually spends a few hours browsing per week suddenly stops viewing webpages during a current week, that person may have an affected mental state. A person who usually browses the Internet in the morning may begin to stay up all night looking at business/economic news and career-related websites because, for example, that person suffered a job loss causing changes in behavior. Pending signs of depression and/or anger, the monitoring mechanism 106 continues monitoring search and browsing logs for additional deviations from normal browsing behavior.

Based upon training data, the training mechanism 112 may generate an example classifier for predicting clinical depression regardless of type. The example classifier may be standardized for a certain demographic group (e.g., gender, age, and/or the like) or across all groups. As one alternative to detecting depression as a general case, the example classifier may be configured to identify a specific type of clinical depression, such as postpartum depression.

Another example implementation configures the example classifier on a plurality of computerized devices operated by a group of patients who may suffer from a same or similar mental illness. Via the server 102, healthcare professionals or other trusted individuals may monitor these patients for symptoms of that mental illness and/or another mental illness. Furthermore, feedback provided by each patient's computer device(s) may improve the example classifier's performance. Example feedback includes information on errors (e.g., false positives/negatives) and correct symptom detections, which may be used to further refine the example classifier.

Alternatively, the monitoring mechanism 106 may be configured to operate on the server 102 instead of or in addition to operating on the user device 104. One alternative implementation monitors data streams uploaded by the user device 104 for user behavioral changes that may affect the user's mental state.

Figure 2:
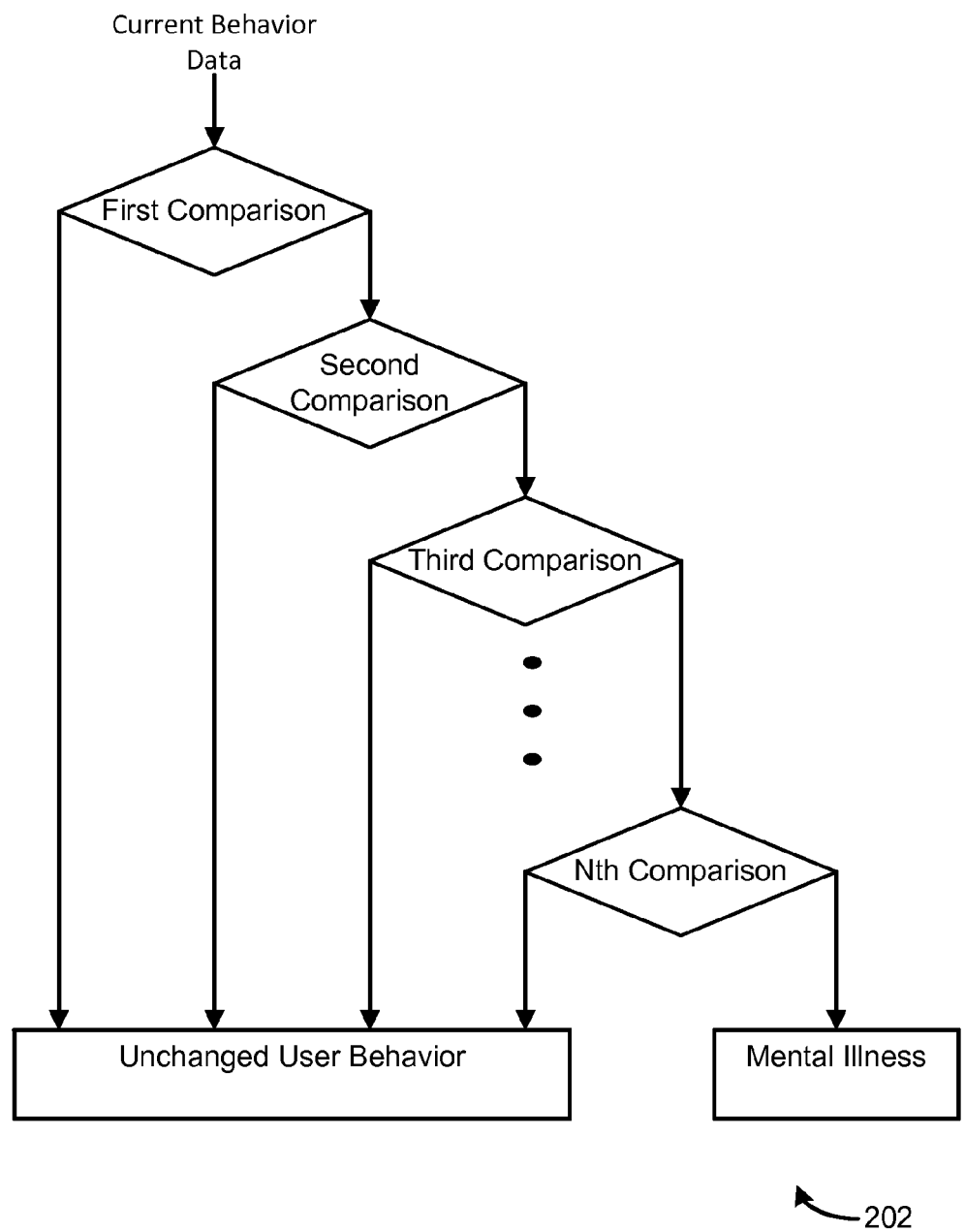
FIG. 2 illustrates one example representation of a prediction model 202 according to one example implementation.

FIG. 2 illustrates one example representation of a prediction model 202 according to one example implementation. While the prediction model 202 resembles a decision tree, it is appreciated that other embodiments of the prediction model 202 use other decision analysis mechanisms, such as utility functions.

The prediction model 202 may be built from various training data. To illustrate one example, a user's online activities may be logged over a period of time and portions of such activities may be annotated to highlight certain behavior features. Based on the presence of these features, the user's behavior may be deemed to exhibit elements of a particular mental state, such as depression. After aggregating each user's feature distribution, a set of expected features for predicting the particular mental state may be determined. Parameters (e.g., thresholds) for evaluating current behavior feature data may be modeled using this set of expected features.

The prediction model 202 may be configured to determine a person's likely mental state based upon that person's interactions with one or more computerized devices, including mobile phones, tablet computers and web servers. Some of these interactions may include communications with other people while other interactions may be search engine queries and recently viewed Internet content. If selected behavior features indicative of a certain mental state can be extracted from the person's interactions, there is high likelihood that the person is actually exhibiting that mental state. An analysis of the selected features may be modeled using a decision mechanism known as a decision tree.

FIG. 2 depicts an example decision tree configured to identify a behavior change likely to affect a user. As described herein, a classifier may employ the example decision tree when monitoring the user's interactions/activities for symptoms of a mental illness. Each step of the decision tree represents a comparison operation between data corresponding to the user's interactions and one or more features. At a first comparison operation, the classifier may label such data as "unchanged user behavior" if a certain key feature is not present; otherwise, a second comparison operation is performed. One example key feature may include usage of threatening language. Regarding the second comparison operation, the classifier may use a threshold value to determine, based upon a number of threatening words entered/spoken, whether the user's behavior changed. The threshold value may represent a normal amount of threatening words for that user and therefore, a statistical significant deviation from that threshold is evidence of an onset of a psychological event.

Figure 3:
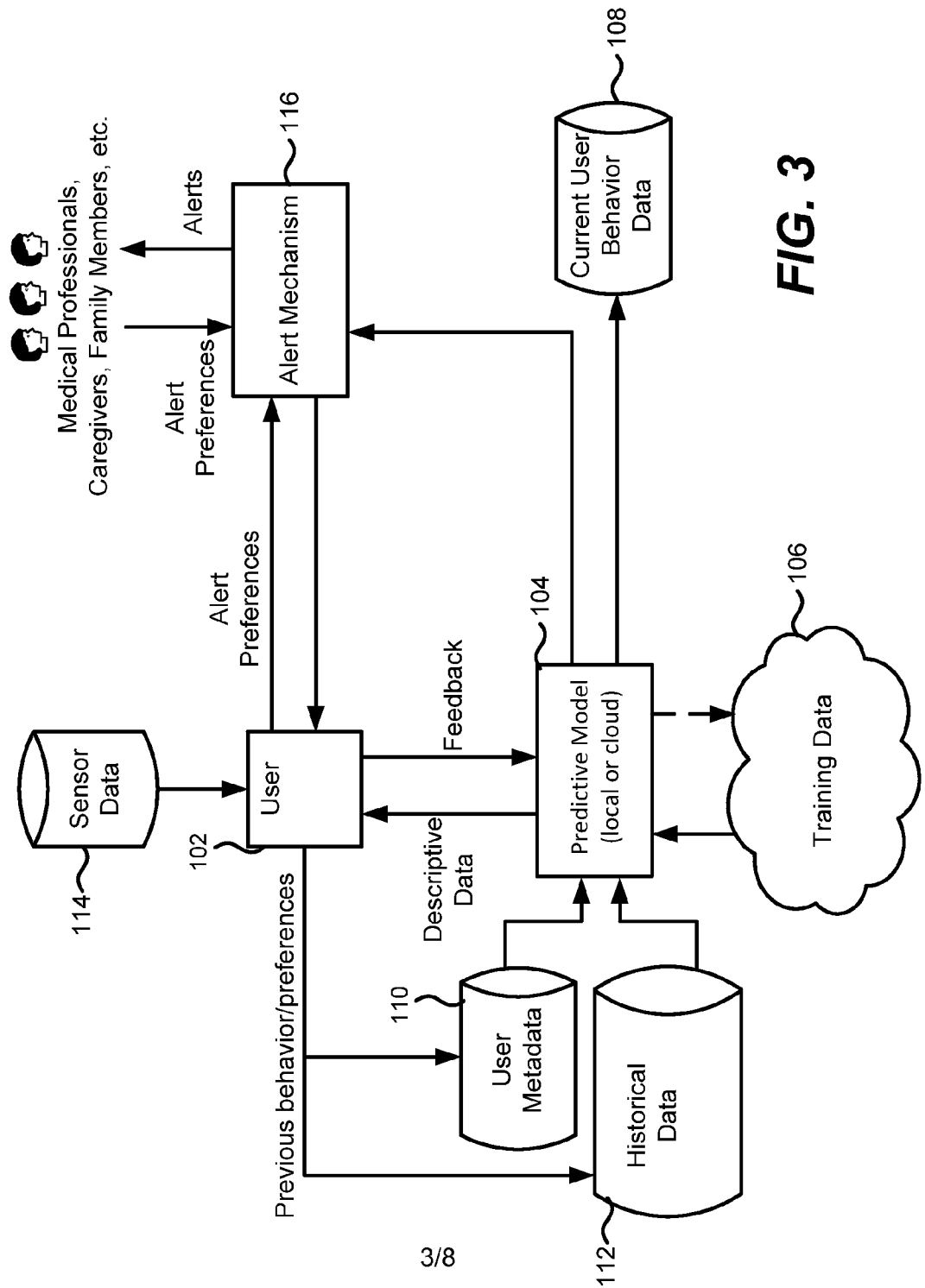
FIG. 3 is a functional block diagram illustrating an example operation of a monitoring mechanism according to one example implementation.

FIG. 3 is a functional block diagram illustrating an example operation of a monitoring mechanism according to one example implementation. As described herein, the monitoring mechanism may run on a computerized device, such as a mobile phone or a desktop computer. In this device, a user 302 installs a classifier with a predictive model 304 that is capable of identifying behavior changes likely to negatively impact the user 302.

According to one example implementation, the predictive model 304 includes a decision tree corresponding to one or more mental states. The decision tree may be generated from training data 306. Examples of the training data 306 include annotated (e.g., labeled) data corresponding to interactions between a plurality of users via various computerized devices. To illustrate one example, a user's online activities may be logged over a period of time and based on the presence of selected features, the user's behavior may be deemed likely to suffer from depressed mental state.

When certain selected features are present in current user behavior data 308, the user 302 may be presented with descriptive data corresponding to a mental state having a highest likelihood. It is appreciated that some mental states are composites of two or more mental states; for example, paranoid schizophrenic is a psychological disorder comprising both paranoia and schizophrenia. Using a number of machine learning techniques, a training mechanism within a centralized server may build a decision tree comprised of branches where each branch represents a condition placed upon one or more features. Enforcing each condition may result in the identification of a mental state having a highest likelihood amongst other mental states. It is appreciated that although the following discussion refers to decision trees, other decision analysis mechanisms can be employed to predict a mental state in light of the user's behavior change.

The monitoring mechanism performs data collection during which available user data is processed and stored, including user metadata 310 and prior online behavior 312 (e.g., historical data). The monitoring mechanism logs queries submitted to search engines, postings to social media portals, content viewed on web pages, and other online activities into the prior online behavior 312. The prior online behavior 312 also may describe the content using categories (e.g., news, sports, and/or the like). The metadata 310 describes the logged data, including hours that the user is online, activity volume, location data, response of the user's friends, tone of voice, and/or the like.

The user 302 provides various feedback for updating the prediction model 304. Example feedback may identify instances of previous psychological events in the prior online behavior 312 enabling the prediction model 304 to be updated with feature information specific to the user 302. The monitoring mechanism may extract key user behavior features related to an example psychological event and adjust the prediction model 304 to recognize such features as a behavior change likely to affect the user 302. For example, if the user 302 provides feedback identifying periods of insomnia caused by stress, the monitoring mechanism may determine one example key feature for such insomnia may be Internet browsing after midnight. Accordingly, the monitoring mechanism modifies the prediction model 304 to recognize future instances of Internet browsing after midnight as a potential bout of insomnia.

One example implementation of the monitoring mechanism also employs various sensor data 314 as a source of user interaction data when predicting the user's mental state. A set of sensor devices may provide the sensor data 314, including voice/speech data recorded by a microphone, video/image data captured by an imaging device, movement data captured by accelerometers and/or the like. To illustrate one example use of the sensor data 314, the monitoring mechanism detects when the user engages in excessive shouting by examining the user's phone calls and comparing related features with the predication model 304. If the user normally restrains their voice volume, sudden excessive shouting may indicate a psychological event.

According to one example implementation, the monitoring mechanism configures an alert component 316 using alert preferences associated with the user 302 and/or alert preferences associated with trusted individuals, such as medical professionals, caregivers, family members and/or the like. The alert preferences may define error preferences, such as an acceptable false negative/false positive ratio for the user, which may be prescribed by a medical provider based on the risk associated with each of these errors.

Figure 4:
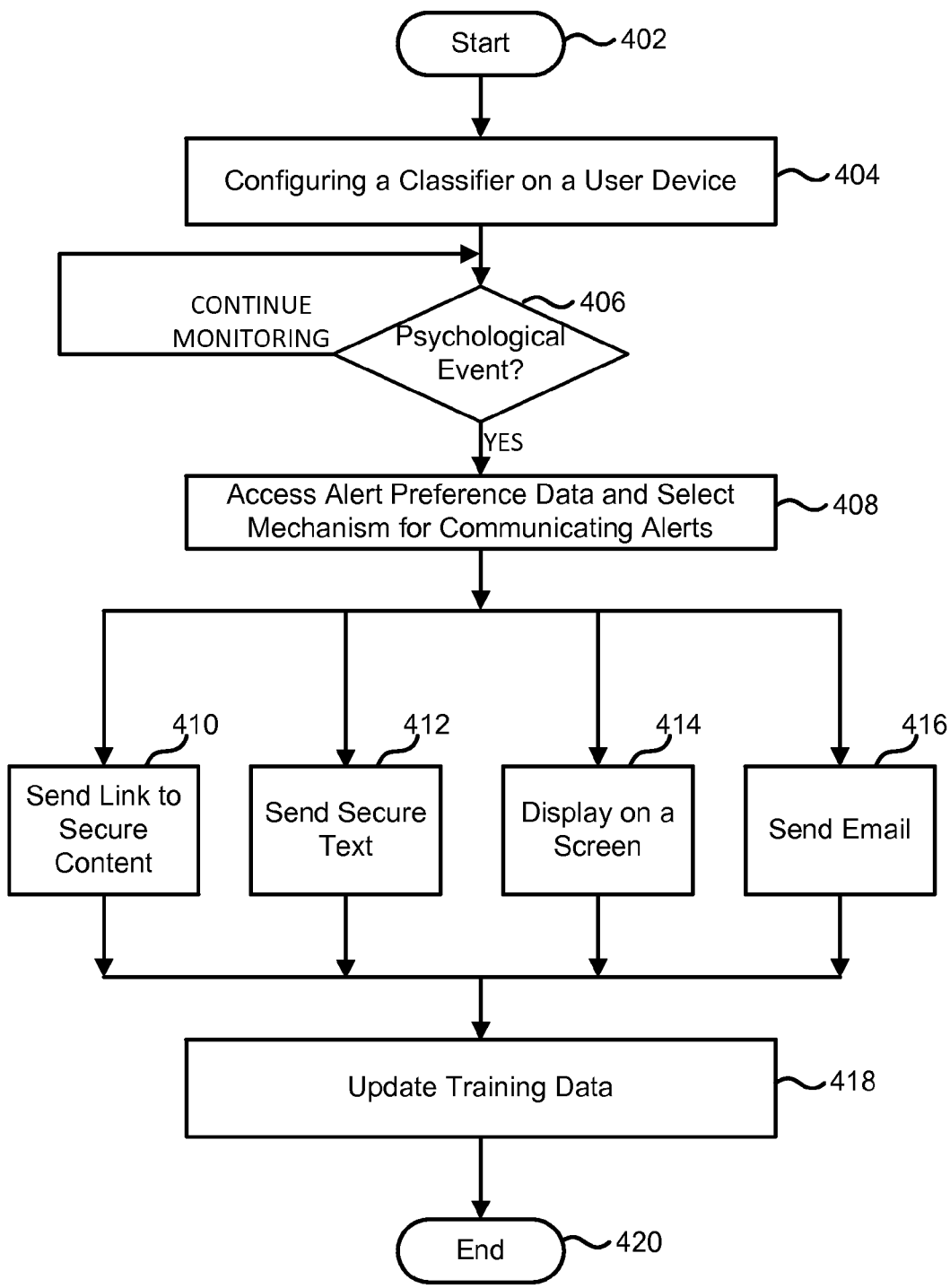
FIG. 4 is a flow diagram illustrating example steps for monitoring a computerized device for psychological events according to one example implementation.

FIG. 4 is a flow diagram illustrating example steps for monitoring a computerized device for psychological events according to one example implementation. One or more hardware/software components (e.g., the monitoring mechanism 106 of FIG. 1 operating on a centralized server) may be configured to perform the example steps. These components may operate in a cloud computing environment (e.g., a public cloud, a private cloud or a hybrid).

Step 402 commences the example steps and proceeds to step 404 where the monitoring mechanism configures a classifier on a user device that identifies changes in the user's behavior based upon user interaction data. The classifiers provide a prediction as to whether the user is experiencing a psychological event or whether he is likely to experience one in the near future (e.g., in the next day, next week and/or the like). Users may establish their user preference with respect to false negative/false positive ratio. In other instances, these preferences may be set by a medical provider or a law enforcement agency, based on the risk associated with each of these errors. A dangerous person, for instance, may be assigned a low ratio and although this setting may lead to more false positives, the risks involved with a positive result may be substantial enough to necessitate that ratio. Furthermore, by operating the monitoring mechanism in a cloud computing environment, the dangerous person is prevented from tampering his or her user device.

Step 406 determines whether that behavior change corresponds to a psychological event. The settings described above also may prescribe procedures/mechanisms for alerting medical providers, law enforcement personnel or other trusted individuals. If the user does not currently exhibit any psychological event, step 406 continues monitoring the user device and waits for an update. The monitoring mechanism may ping a component running on the user device for the update. If the monitoring mechanism predicts a psychological event, step 406 proceeds to step 408. Step 408 accesses alert preference data and selects one or more mechanisms for securely communicating one or more alerts to trusted individuals. Step 410 represents one example alert mechanism that securely alerts a trusted family member/healthcare professional by sending a link to secure content, such as a hyperlink to a secure web page where descriptive data for the psychological event is displayed to that trusted individual. The secure web page may be password-protected web site on which the trusted individual needs to enter a correct password in order to view the descriptive data.

Step 412 represents another example alert mechanism that sends secure text to the trusted individual. For instance, the other example alert mechanism may encrypt the descriptive data using an applicable cryptographic scheme and communicate a message comprising encrypted text. The trusted individual may be allowed to view an unencrypted version of the descriptive data after providing a secret key.

Step 414 represents an example alert mechanism that displays the descriptive data on a computerized device screen. It is appreciated that this alert mechanism is unsecure and anyone capable of viewing the computerized device screen also may view the descriptive data. Step 416 represents a fourth alert mechanism configured to send an email to the trusted individual.

Step 418 updates training data for the classifier to reflect the psychological event detection. Over time, the classifier is adapted to the user's behavior by providing feedback (e.g., as to when the user did or did not experience an event), and this feedback may be used to retrain the classifiers. Step 420 terminates the example steps depicted in FIG. 4.

Figure 5:
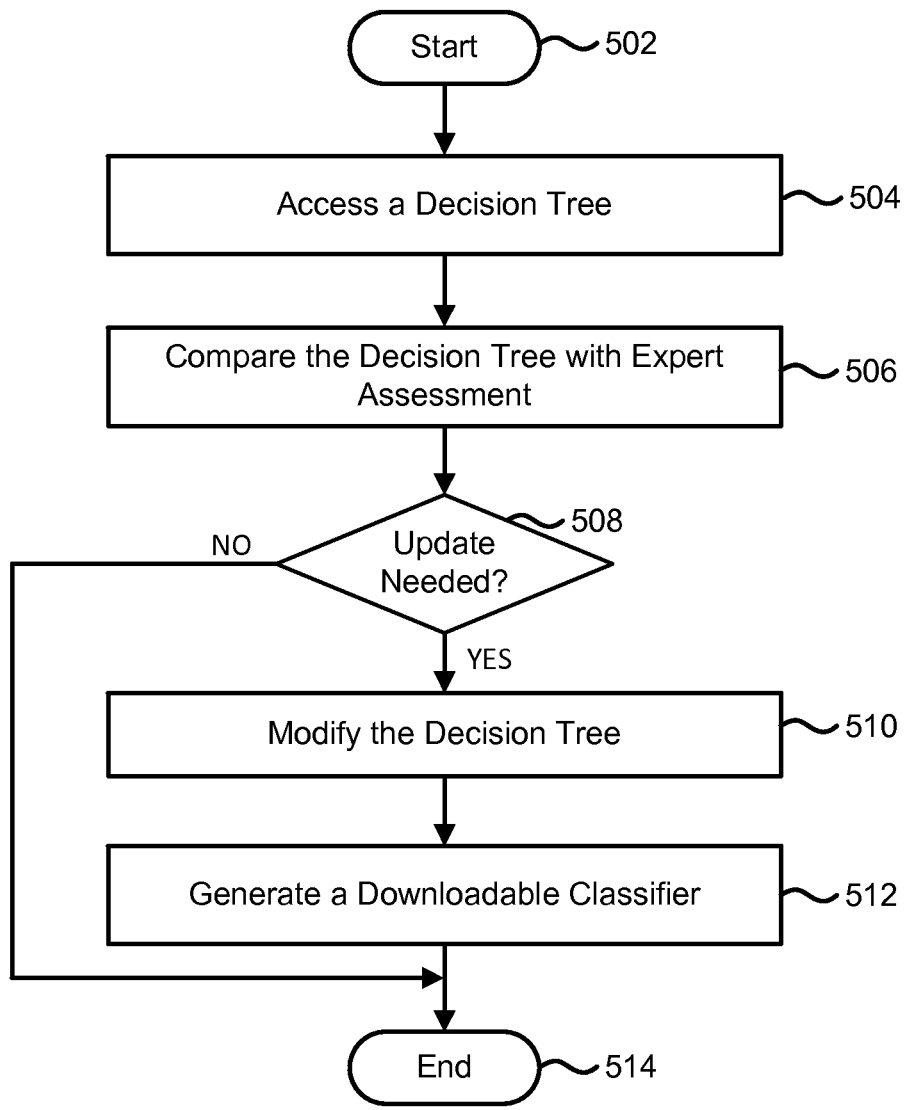
FIG. 5 is a flow diagram illustrating example steps for generating a classifier for predicting psychological events according to one example implementation.

FIG. 5 is a flow diagram illustrating example steps for generating a classifier for predicting psychological events according to one example implementation. One or more hardware/software components (e.g., a training mechanism, such as the training mechanism 112 of FIG. 1) may be configured to perform the example steps. Step 502 commences the example steps and proceeds to step 504 where a prediction model known as a decision tree is accessed. As described herein, the prediction model may be configured to identify behavior changes being likely to affect a user's mental state. Although the following description refers to decision trees, it is appreciated that the example steps are applicable to any prediction model. Some embodiments envisioned by the present disclosure may implement prediction models as utility functions, Bayesian classifiers, and/or other statistical mechanisms for decision analysis.

Step 506 compares the decision tree with an expert assessment. One example implementation allows a mental health expert to improve the decision tree when, for instance, mislabeling occurs by providing the expert assessment of the decision tree. The mental health expert may annotate, add/remove, and/or modify the decision tree. For example, a condition may be added to the decision tree for a new feature. Step 508 determines whether to use the expert assessment for updating the decision tree. As one example, step 508 updates the decision tree if a number of errors (e.g., false positives/false negatives) exceeds an acceptable amount and/or if adopting the expert's assessment is likely to increase a detection success rate.

Step 510 modifies the decision tree by, for example, modifying at least one comparison operation. Step 510 may lower a particular feature's threshold value in order to mitigate false negatives. As one alternative, step 510 may modify the decision tree with additional features in order to reduce false positives. Step 512 generates a classifier based upon the modified decision tree. This classifier may be downloadable from a server or configured to operate on that server as a network service. As an alternative, the user's computerized device may generate the classifier from the prediction model instead of downloading a copy of the classifier from the server.

One example implementation may designate the classifier as an initial classifier for each user individually or within a group. Over time, users will be able to adapt the classifier to the user's behavior by providing feedback indicating instances when they did or did not experience a psychological event, which may be used to retrain the downloadable classifier for that specific event. If permitted, such feedback may periodically be communicated to a centralized server for improving the downloadable classifier. Optionally, the user's feedback may continuously update the classifier operating within his or her computerized device. Step 514 terminates the example steps of FIG. 5. Note that instead of modifying a tree, occasionally a new instance of that tree may be rebuilt from scratch as more and more training data become available.

Figure 6:
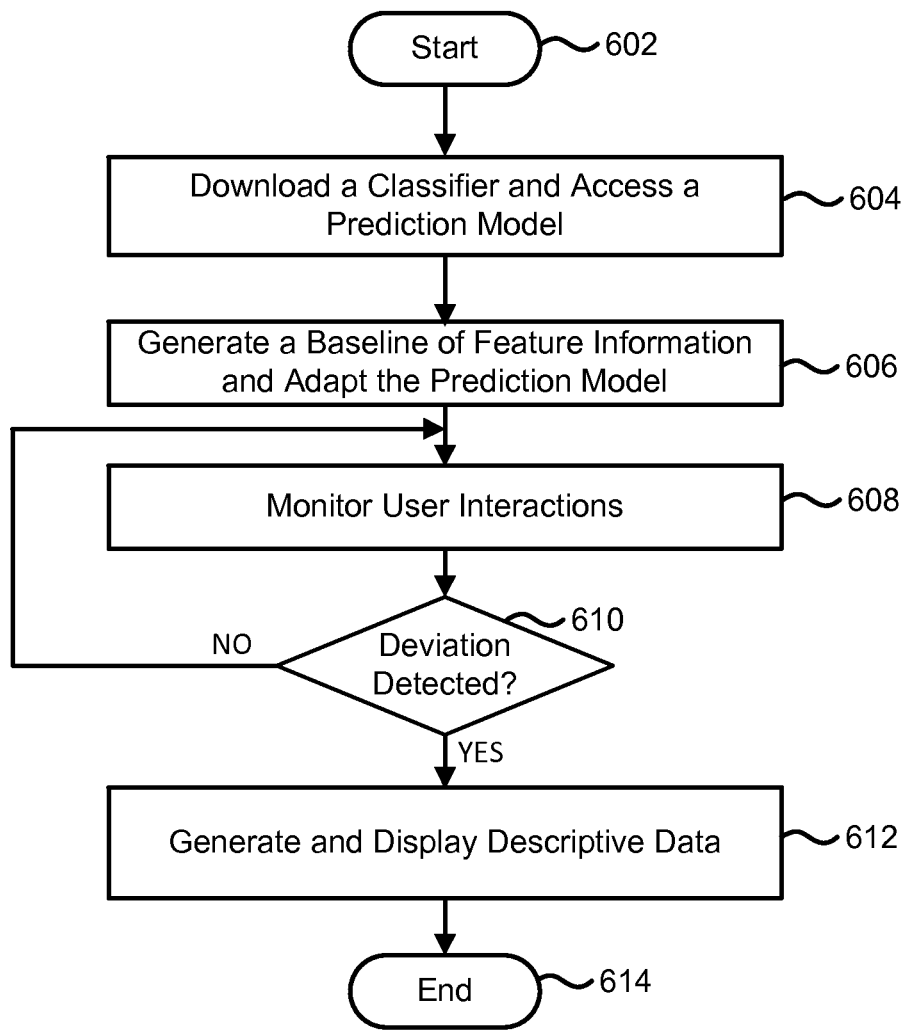
FIG. 6 is a flow diagram illustrating example steps for identifying a behavior change likely to affect a user according to one example implementation.

FIG. 6 is a flow diagram illustrating example steps for identifying a behavior change likely to affect a user according to one example implementation. One or more hardware/software components (e.g., an operating system component, such as the monitoring mechanism 106 of FIG. 1) may be configured to perform the example steps. Step 602 commences the example steps and proceeds to step 604, which downloads a classifier and accesses a prediction model. A centralized server may provide a set of classifiers for any type of mental health issues, including mood disorders and postpartum depression.

Step 606 generates a baseline of feature information associated with the user's behavior and adapts the prediction model to that baseline. The baseline includes statistical distributions of expected features for normal or acceptable user behavior. One example implementation of a user-customized prediction model includes conditions configured with expected feature distributions. This is, in part, because detecting an absence of or a statistical significant deviation an expected feature distribution represents a strong likelihood that the user's behavior has changed is or likely to change from normal or acceptable behavior.

Step 608 monitors user interactions via the computerized device. Step 610 determines whether current user behavior deviates from the baseline in order to recognize potential user behavior changes. Step 612 generates and displays descriptive data to the user that corresponds to a mental state having a highest likelihood based upon previous user behavior. Step 614 terminates the example steps of FIG. 6.

As can be seen, there is provided a technology for monitoring user behavior on a computerized device. The technology facilitates monitoring of a patient at home, in between visits to a healthcare professional or treatment facility and/or without needing a personal caregiver.

Example Networked and Distributed Environments

One of ordinary skill in the art can appreciate that the various embodiments and methods described herein can be implemented in connection with any computer or other client or server device, which can be deployed as part of a computer network or in a distributed computing environment, and can be connected to any kind of data store or stores. In this regard, the various embodiments described herein can be implemented in any computer system or environment having any number of memory or storage units, and any number of applications and processes occurring across any number of storage units. This includes, but is not limited to, an environment with server computers and client computers deployed in a network environment or a distributed computing environment, having remote or local storage.

Distributed computing provides sharing of computer resources and services by communicative exchange among computerized devices and systems. These resources and services include the exchange of information, cache storage and disk storage for objects, such as files. These resources and services also include the sharing of processing power across multiple processing units for load balancing, expansion of resources, specialization of processing, and the like. Distributed computing takes advantage of network connectivity, allowing clients to leverage their collective power to benefit the entire enterprise. In this regard, a variety of devices may have applications, objects or resources that may participate in the resource management mechanisms as described for various embodiments of the subject disclosure.

Figure 7:
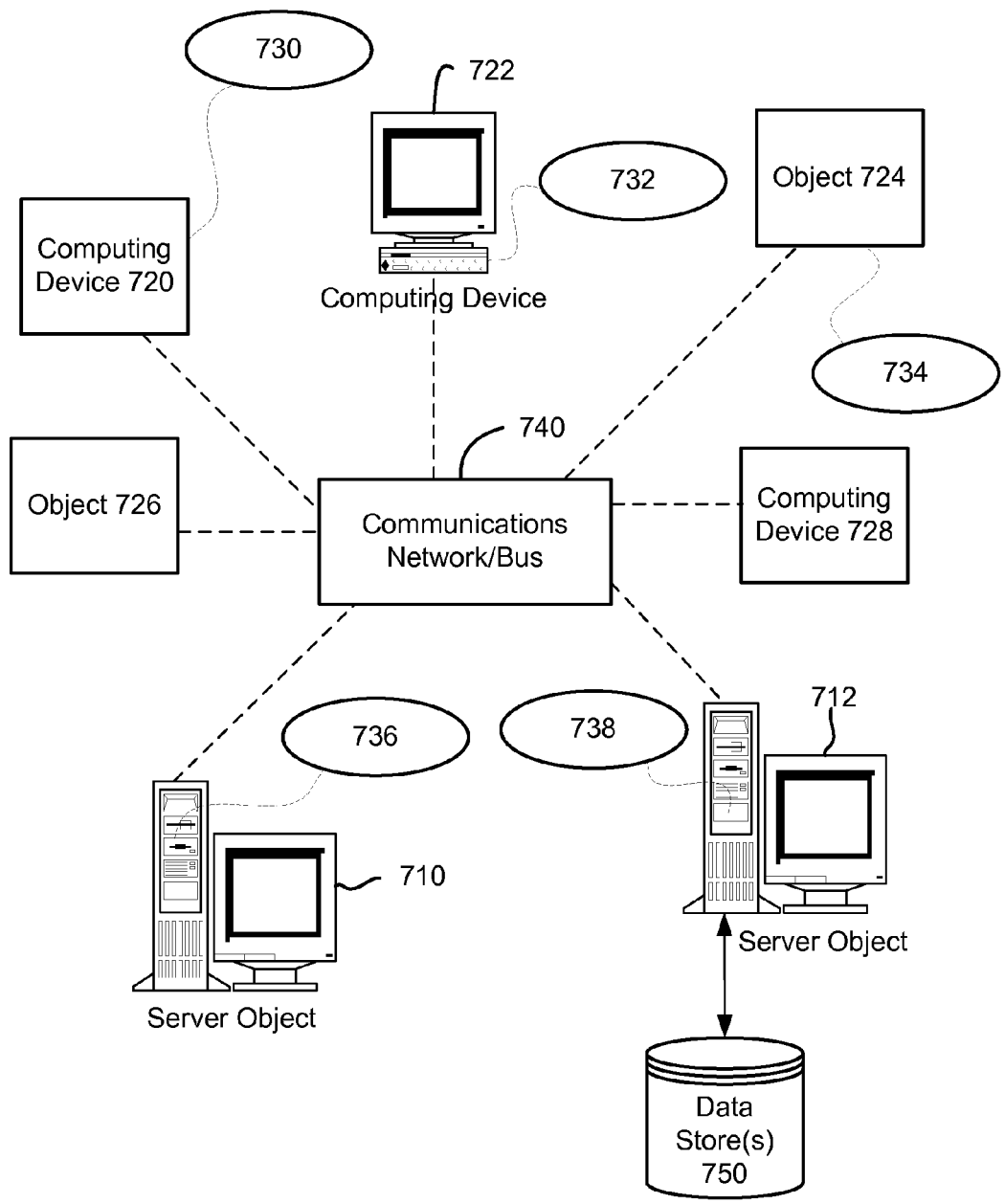
FIG. 7 is a block diagram representing example non-limiting networked environments in which various embodiments described herein can be implemented.

FIG. 7 provides a schematic diagram of an example networked or distributed computing environment. The distributed computing environment comprises computing objects 710, 712, etc., and computing objects or devices 720, 722, 724, 726, 728, etc., which may include programs, methods, data stores, programmable logic, etc. as represented by example applications 730, 732, 734, 736, 738. It can be appreciated that computing objects 710, 712, etc. and computing objects or devices 720, 722, 724, 726, 728, etc. may comprise different devices, such as personal digital assistants (PDAs), audio/video devices, mobile phones, MP3 players, personal computers, laptops, etc.

Each computing object 710, 712, etc. and computing objects or devices 720, 722, 724, 726, 728, etc. can communicate with one or more other computing objects 710, 712, etc. and computing objects or devices 720, 722, 724, 726, 728, etc. by way of the communications network 740, either directly or indirectly. Even though illustrated as a single element in FIG. 7, communications network 740 may comprise other computing objects and computerized devices that provide services to the system of FIG. 7, and/or may represent multiple interconnected networks, which are not shown. Each computing object 710, 712, etc. or computing object or device 720, 722, 724, 726, 728, etc. can also contain an application, such as applications 730, 732, 734, 736, 738, that might make use of an API, or other object, software, firmware and/or hardware, suitable for communication with or implementation of the application provided in accordance with various embodiments of the subject disclosure.

There are a variety of systems, components, and network configurations that support distributed computing environments. For example, computing systems can be connected together by wired or wireless systems, by local networks or widely distributed networks. Currently, many networks are coupled to the Internet, which provides an infrastructure for widely distributed computing and encompasses many different networks, though any network infrastructure can be used for example communications made incident to the systems as described in various embodiments.

Thus, a host of network topologies and network infrastructures, such as client/server, peer-to-peer, or hybrid architectures, can be utilized. The "client" is a member of a class or group that uses the services of another class or group to which it is not related. A client can be a process, e.g., roughly a set of instructions or tasks, that requests a service provided by another program or process. The client process utilizes the requested service without having to "know" any working details about the other program or the service itself.

In a client/server architecture, particularly a networked system, a client is usually a computer that accesses shared network resources provided by another computer, e.g., a server. In the illustration of FIG. 7, as a non-limiting example, computing objects or devices 720, 722, 724, 726, 728, etc. can be thought of as clients and computing objects 710, 712, etc. can be thought of as servers where computing objects 710, 712, etc., acting as servers provide data services, such as receiving data from client computing objects or devices 720, 722, 724, 726, 728, etc., storing of data, processing of data, transmitting data to client computing objects or devices 720, 722, 724, 726, 728, etc., although any computer can be considered a client, a server, or both, depending on the circumstances.

A server is typically a remote computer system accessible over a remote or local network, such as the Internet or wireless network infrastructures. The client process may be active in a first computer system, and the server process may be active in a second computer system, communicating with one another over a communications medium, thus providing distributed functionality and allowing multiple clients to take advantage of the information-gathering capabilities of the server.

In a network environment in which the communications network 740 or bus is the Internet, for example, the computing objects 710, 712, etc. can be Web servers with which other computing objects or devices 720, 722, 724, 726, 728, etc. communicate via any of a number of known protocols, such as the hypertext transfer protocol (HTTP). Computing objects 710, 712, etc. acting as servers may also serve as clients, e.g., computing objects or devices 720, 722, 724, 726, 728, etc., as may be characteristic of a distributed computing environment. Computing object 712, for example, acting as a server provides client computing objects or devices 720, 722, 724, 726, 728, etc. with access to storage resources within data store(s) 750.

Example Computerized Device

As mentioned, advantageously, the techniques described herein can be applied to any device. It can be understood, therefore, that handheld, portable and other computerized devices and computing objects of all kinds are contemplated for use in connection with the various embodiments. Accordingly, the below general purpose remote computer described below in FIG. 8 is but one example of a computerized device.

Embodiments can partly be implemented via an operating system, for use by a developer of services for a device or object, and/or included within application software that operates to perform one or more functional aspects of the various embodiments described herein. Software may be described in the general context of computer executable instructions, such as program modules, being executed by one or more computers, such as client workstations, servers or other devices. Those skilled in the art will appreciate that computer systems have a variety of configurations and protocols that can be used to communicate data, and thus, no particular configuration or protocol is considered limiting.

Figure 8:
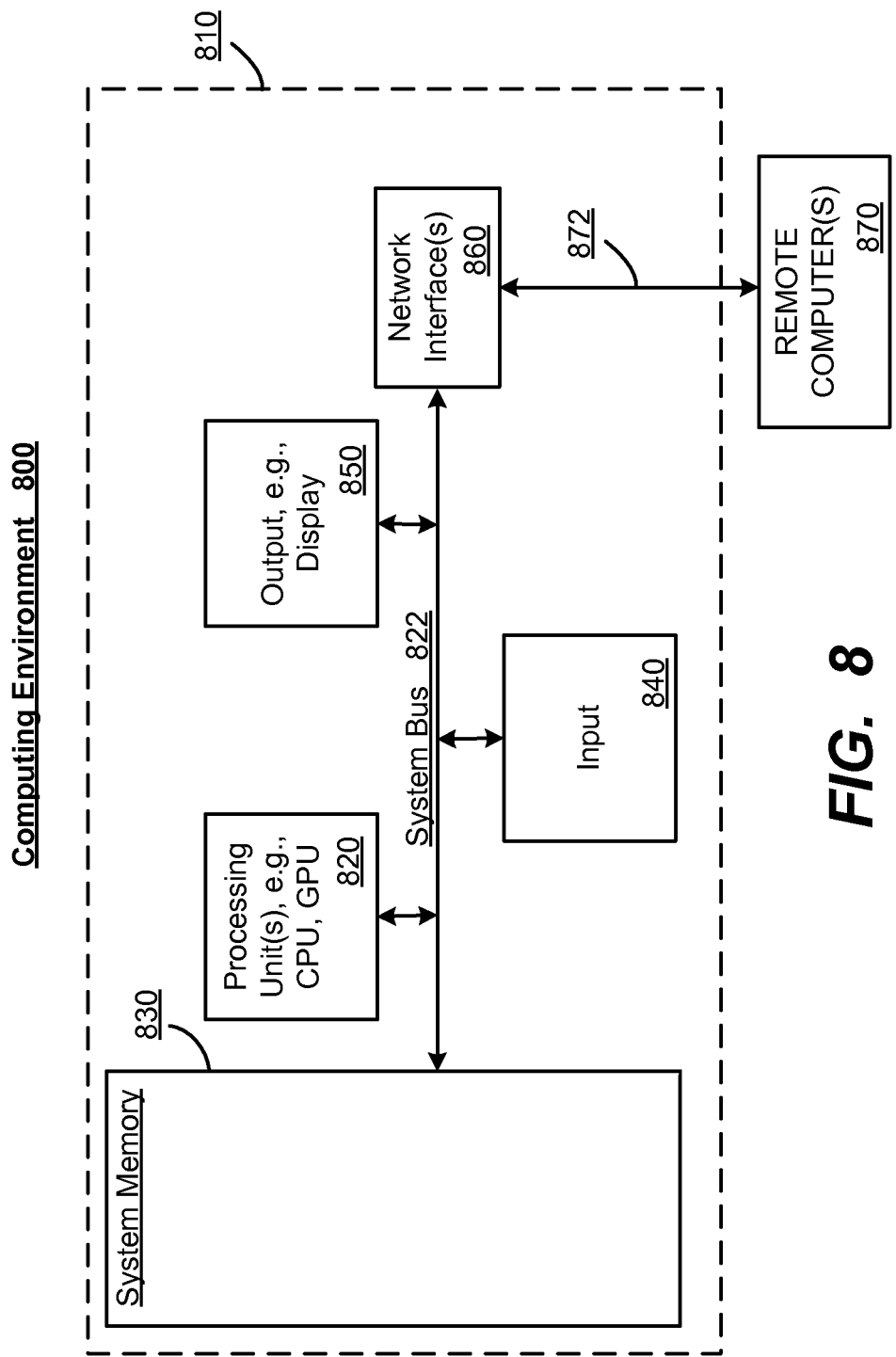
FIG. 8 is a block diagram representing an example non-limiting computing system or operating environment in which one or more aspects of various embodiments described herein can be implemented.

FIG. 8 thus illustrates an example of a suitable computing system environment 800 in which one or aspects of the embodiments described herein can be implemented, although as made clear above, the computing system environment 800 is only one example of a suitable computing environment and is not intended to suggest any limitation as to scope of use or functionality. In addition, the computing system environment 800 is not intended to be interpreted as having any dependency relating to any one or combination of components illustrated in the example computing system environment 800.

With reference to FIG. 8, an example remote device for implementing one or more embodiments includes a general purpose computerized device in the form of a computer 810. Components of computer 810 may include, but are not limited to, a processing unit 820, a system memory 830, and a system bus 822 that couples various system components including the system memory to the processing unit 820.

Computer 810 typically includes a variety of computer readable media and can be any available media that can be accessed by computer 810. The system memory 830 may include computer storage media in the form of volatile and/or nonvolatile memory such as read only memory (ROM) and/or random access memory (RAM). By way of example, and not limitation, system memory 830 may also include an operating system, application programs, other program modules, and program data.

A user can enter commands and information into the computer 810 through input devices 840. A monitor or other type of display device is also connected to the system bus 822 via an interface, such as output interface 850. In addition to a monitor, computers can also include other peripheral output devices such as speakers and a printer, which may be connected through output interface 850.

The computer 810 may operate in a networked or distributed environment using logical connections to one or more other remote computers, such as remote computer 870. The remote computer 870 may be a personal computer, a server, a router, a network PC, a peer device or other common network node, or any other remote media consumption or transmission device, and may include any or all of the elements described above relative to the computer 810. The logical connections depicted in FIG. 8 include a network 872, such local area network (LAN) or a wide area network (WAN), but may also include other networks/buses. Such networking environments are commonplace in homes, offices, enterprise-wide computer networks, intranets and the Internet.

As mentioned above, while example embodiments have been described in connection with various computerized devices and network architectures, the underlying concepts may be applied to any network system and any computerized device or system in which it is desirable to improve efficiency of resource usage.

Also, there are multiple ways to implement the same or similar functionality, e.g., an appropriate API, tool kit, driver code, operating system, control, standalone or downloadable software object, etc. which enables applications and services to take advantage of the techniques provided herein. Thus, embodiments herein are contemplated from the standpoint of an API (or other software object), as well as from a software or hardware object that implements one or more embodiments as described herein. Thus, various embodiments described herein can have aspects that are wholly in hardware, partly in hardware and partly in software, as well as in software.

The word "exemplary" is used herein to mean serving as an example, instance, or illustration. For the avoidance of doubt, the subject matter disclosed herein is not limited by such examples. In addition, any aspect or design described herein as "exemplary" is not necessarily to be construed as preferred or advantageous over other aspects or designs, nor is it meant to preclude equivalent exemplary structures and techniques known to those of ordinary skill in the art. Furthermore, to the extent that the terms "includes," "has," "contains," and other similar words are used, for the avoidance of doubt, such terms are intended to be inclusive in a manner similar to the term "comprising" as an open transition word without precluding any additional or other elements when employed in a claim.

As mentioned, the various techniques described herein may be implemented in connection with hardware or software or, where appropriate, with a combination of both. As used herein, the terms "component," "module," "system" and the like are likewise intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers.

The aforementioned systems have been described with respect to interaction between several components. It can be appreciated that such systems and components can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it can be noted that one or more components may be combined into a single component providing aggregate functionality or divided into several separate sub-components, and that any one or more middle layers, such as a management layer, may be provided to communicatively couple to such sub-components in order to provide integrated functionality. Any components described herein may also interact with one or more other components not specifically described herein but generally known by those of skill in the art.

In view of the example systems described herein, methodologies that may be implemented in accordance with the described subject matter can also be appreciated with reference to the flowcharts of the various figures. While for purposes of simplicity of explanation, the methodologies are shown and described as a series of blocks, it is to be understood and appreciated that the various embodiments are not limited by the order of the blocks, as some blocks may occur in different orders and/or concurrently with other blocks from what is depicted and described herein. Where non-sequential, or branched, flow is illustrated via flowchart, it can be appreciated that various other branches, flow paths, and orders of the blocks, may be implemented which achieve the same or a similar result. Moreover, some illustrated blocks are optional in implementing the methodologies described hereinafter.

CONCLUSION

While the invention is susceptible to various modifications and alternative constructions, certain illustrated embodiments thereof are shown in the drawings and have been described above in detail. It should be understood, however, that there is no intention to limit the invention to the specific forms disclosed, but on the contrary, the intention is to cover all modifications, alternative constructions, and equivalents falling within the spirit and scope of the invention.

In addition to the various embodiments described herein, it is to be understood that other similar embodiments can be used or modifications and additions can be made to the described embodiment(s) for performing the same or equivalent function of the corresponding embodiment(s) without deviating therefrom. Still further, multiple processing chips or multiple devices can share the performance of one or more functions described herein, and similarly, storage can be effected across a plurality of devices. Accordingly, the invention is not to be limited to any single embodiment, but rather is to be construed in breadth, spirit and scope in accordance with the appended claims.

What is claimed is:

1. A method performed at least in part on at least one processor comprising:

establishing, by a monitoring component implemented on the at least one processor, a behavior baseline for a user;

obtaining, by the monitoring component, user interaction data comprising one or more of search engine queries and social media postings of the user;

accessing a predictive model corresponding to features of at least one mental state;

comparing the predictive model with the obtained user interaction data to identify a current mental state of the user based on the features of the at least one mental state and the one or more of the search engine queries and social media postings of the user; and in response to identifying a deviation between the identified current mental state and the established behavior baseline, generating description data for the identified current mental state.

2. The method of claim 1 further comprising:
using the predictive model to monitor for symptoms of a mental illness.

3. The method of claim 1 further comprising:
communicating an alert corresponding to the identified current mental state.

4. The method of claim 1 further comprising:
configuring the predictive model based upon user preferences associated with prediction error data.

5. The method of claim 1 wherein comparing the predictive model with the obtained user interaction data to identify the current mental state of the user further comprises extracting feature information from the user interaction data.

6. The method of claim 1, wherein the user interaction data further comprises sensor data obtained from one or more sensors, the method further comprising:
extracting feature information from the user interaction data to compare with the predictive model.

7. The method of claim 1 further comprising:
selecting a future mental state from an expected set of features that corresponds to a current deviation from the behavior baseline.

8. In a computing environment, a computerized device or a configuration of coupled computerized devices, comprising:
a prediction model corresponding to at least one mental state; and
a monitoring mechanism configured to:
obtain user interaction data comprising one or more of search engine queries and social media postings of a user;
extract features from the user interaction data using the prediction model;
determine whether a psychological event is evident from the extracted features;
responsive to a determination that the psychological event is evident, generate a secure alert corresponding to the psychological event.

9. The computerized device or the configuration of coupled computerized devices of claim 8, wherein the monitoring mechanism is further configured to:
communicate encrypted descriptive data corresponding to the psychological event.

10. The computerized device or the configuration of coupled computerized devices of claim 8, wherein the monitoring mechanism is further configured to:
process historical data corresponding to user behavior; and
adapt the prediction model to the user behavior.

11. The computerized device or the configuration of coupled computerized devices of claim 8, wherein the monitoring mechanism is further configured to:
communicate a message comprising a link to a protected web page for displaying descriptive data corresponding to the psychological event.

12. The computerized device or the configuration of coupled computerized devices of claim 8, wherein the monitoring mechanism is further configured to:
access a classifier built upon the prediction model; and
customize the classifier using user preference data.

13. The computerized device or the configuration of coupled computerized devices of claim 8, wherein the monitoring mechanism is further configured to:
communicate feedback to a server for updating the prediction model.

14. The computerized device or the configuration of coupled computerized devices of claim 8, wherein at least part of the monitoring mechanism is further configured to operate on a server.

15. The computerized device or the configuration of coupled computerized devices of claim 8, wherein the monitoring mechanism is further configured to:
update the prediction model with feedback related to previous instances of psychological events.

16. One or more computer storage media having computer-executable instructions, which on execution by a computer cause the computer to perform operations, comprising:
generating at least one classifier built from at least one prediction model associated with at least one mental state;
configuring the at least one classifier to monitor user interaction data for a symptom of a mental illness, the user interaction data including data comprising one or more of search engine queries and social media postings of a user via a user device; and
processing feedback from the user device to update the at least one prediction model based at least in part on the user interaction data, including the data comprising the one or more of the search engine queries and the social media postings of the user.

17. The one or more computer storage media of claim 16, wherein configuring the at least one classifier further comprises:
configuring the at least one classifier on a plurality of computerized devices corresponding to a group of patients.

18. The one or more computer storage media of claim 16 having further computer-executable instructions comprising:
communicating a secure alert according to alert preference data.

19. The one or more computer storage media of claim 16 having further computer-executable instructions comprising:
accessing training data corresponding to user behavior of at least one similar user; and
using the training data as an initial prediction model for generating the at least one classifier.

20. The one or more computer storage media of claim 16 having further computer-executable instructions comprising:
adjusting the prediction model based upon an expert assessment.

* * * * *